United States Patent

Chopra et al.

[11] Patent Number: 5,891,834
[45] Date of Patent: Apr. 6, 1999

[54] COMPOSITION

[75] Inventors: Suman Kumar Chopra, Dayton; Thomas Gregory Polefka, Somerset; Ravi Subramanyam, Belle Mead, all of N.J.

[73] Assignee: Colgate Palmolive Company

[21] Appl. No.: 716,589

[22] Filed: Sep. 18, 1996

Related U.S. Application Data

[60] Provisional application No. 60/003,992 Sep. 19, 1995.

[51] Int. Cl.$^6$ ..................................................... C11D 9/00
[52] U.S. Cl. ........................ 510/141; 510/150; 510/152; 510/469
[58] Field of Search ................................... 510/131, 133, 510/150, 152, 469, 141

[56] References Cited

U.S. PATENT DOCUMENTS

| | | |
|---|---|---|
| 3,511,783 | 5/1970 | Waring . |
| 3,536,628 | 10/1970 | Lanecashire . |
| 3,694,367 | 9/1972 | Peters et al. . |
| 3,723,329 | 3/1973 | Mold . |
| 3,959,168 | 5/1976 | Germscheid et al. ................... 252/180 |
| 3,965,024 | 6/1976 | Schmadel et al. ...................... 510/318 |
| 3,991,001 | 11/1976 | Srinivasan et al. . |
| 4,169,074 | 9/1979 | Conrad et al. ........................... 510/341 |
| 4,171,278 | 10/1979 | Andree et al. ........................... 510/316 |
| 4,224,308 | 9/1980 | Gaffar et al. .............................. 424/49 |
| 4,224,309 | 9/1980 | Gaffar, et al. ............................. 424/54 |
| 4,704,223 | 11/1987 | Gupta et al. . |
| 4,839,075 | 6/1989 | Puchta et al. ............................ 510/332 |

FOREIGN PATENT DOCUMENTS

| | | |
|---|---|---|
| 2207983 | 6/1974 | France . |
| 1045373 | 4/1957 | Germany . |
| 1617180 | 12/1965 | Germany . |
| 1272486 | 4/1972 | United Kingdom . |

OTHER PUBLICATIONS

CA 57445k, Superfatted toilet soap, Smith et al, FR 2,008916 Jan. 30, 1970.
CA 84:76184t, Superfat Detergent Composition, Neth App 74 12,566.
CA 60507y, Superfatted Soap Bars, Meye, et al, German Offen 2,308,098, Aug. 22, 1974.
CA 40628h Superfatted Soap Cakes Prepared by use of Phosphorous Compounds, Armstrong, FR 1,530952 Jun. 28, 1968.
CA 116: 43428b, Preparation of Superfatted Beauty Soap, AAI Duosheng, Riyong Huaxue Gongye 1991, (3), 130–2.

*Primary Examiner*—Jacqueline V. Howard
*Assistant Examiner*—Cephia D. Toomer
*Attorney, Agent, or Firm*—Martin B. Barancik

[57] ABSTRACT

A personal cleansing composition comprising
  a. at least about one wt % of soap, and
  b. a sufficient amount of a compound to provide at least about 0.03 wt. % of a free fatty carboxylic acid, said compound of the formula

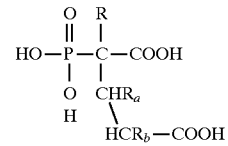

wherein R is hydrogen or $CH_2COOH$, $R_a$ is hydrogen or carboxyl, and $R_b$ is hydrogen or methyl provided that when R is hydrogen, then $R_a$ is carboxyl and when R is $CH_2COOH$ then $R_a$ is hydrogen.

18 Claims, No Drawings

COMPOSITION

This application claims benefit of Provisional Appln 60/003,992, filed Sep. 19, 1995.

BACKGROUND OF THE INVENTION

Soaps have been used for hundreds of years to remove soil from skin. Continual efforts have been made to improve the actions of soaps while increasing mildness, shelf life, lather and the like.

A new method has been discovered which can bring about a combination of increased lather, superfatting, and shelf life compared with previously modified compositions. This is accomplished by the presence in the solid or liquid formulation of a member of a specific family of compounds which has at least two of these effects.

SUMMARY OF THE INVENTION

In accordance with the invention, there is a personal cleansing composition comprising a. at least about 1 wt. % of soap, and b. a sufficient amount of a compound to provide at least about 0.03 wt. % of a free fatty carboxylic acid, said compound of the formula

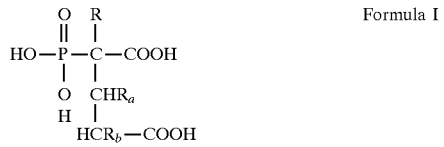

Formula I wherein R is hydrogen, or $CH_2COOH$ and $R_a$ is hydrogen or carboxyl, and $R_b$ is hydrogen or methyl provided that when R is hydrogen, $R_a$ is carboxy and when R is $CH_2COOH$ then $R_a$ is hydrogen.

DETAILED DESCRIPTION OF THE INVENTION

The 2- phosphonobutane- 1,2,4-tricarboxylic acid compounds of FIG. 1 are known in the art as anti calculus agents in oral compositions. The typical excipients in oral compositions would be present in such oral care formulations, for example an oral flavoring agent, an abrasive, a fluoridating agent and the like. However, absent from such an oral composition would be a material which would bring about an unpleasant taste and which would be difficult if not impossible to mask by any reasonable level of flavorant. Examples of such materials would be ordinary soaps such as long chain alkyl or alkenyl, preferably normal, carboxylic acid salts such as sodium, potassium, ammonium or substituted ammonium. Since the compositions of this invention are not to be ingested, it is preferable that the flavoring agent be absent from this inventive composition or at most, a less than non soap masking quantity be present, assuming that such a masking level could be achieved. Additionally, it is preferred that neither a fluoridating agent nor an abrasive agent be present in the personal care, non-oral or ingested compositions of this invention.

It has now been found that when a 2-phosphonobutane-1,2,4 tricarboxylic acid (PBCA) compound or 1-phosphonopropane-1,2,3-tricarboxylic acid (PPTC) compound, preferably PBCA of FIG. 1, is contacted with a soap in the presence of water, at lease three moles of free fatty acid are liberated from the soap for every mole of PBCA or PPTC present. The phosphonobutane becomes a salt and is highly effective as a preservative in the liquid or solid personal care cleansing composition. It is believed, although the applicants do not wish to be bound thereby, that PBCA and PPTC compounds function as a chelating agent for those small quantities of metals present that catalyze oxidation of long chain hydrocarbon containing compounds, particularly those having unsaturation. Therefore, the presence of the soap and the tricarboxylic acid brings about an excellent, in situ means of generating both a superfatting and a preservative effect for an ordinary soap containing personal care composition.

The quantity of the Formula 1 compounds present in the personal cleansing composition is enough to generate at least about 0.03 wt. % of free fatty carboxylic acids in the composition after interaction with the soap present in the composition. Quantities of generated free fatty carboxylic acid minimums in like compositions can be at least about 0.1, 1.0, 2.0, 5.0, 7.0 and 10.0 wt. % of the composition. Up to about 25 wt. % of the composition, preferably no more than about 20 wt. % of the composition are free fatty carboxylic acids. The free fatty carboxylic acid generated does not differ significantly in structure from the anionic portion of the soap present in the composition. The free fatty acid generated therefore, is substantially alkyl of about 10 to about 20 carbon atoms and normal as opposed to branched. Of course the total free fatty acid in the composition need not be generated solely from the interaction of the PBCA or PPTC but can be partially due to the addition of ordinary free fatty acids such as myristic, palmitic, and stearic or in-situ superfatting from citric acid.

The quantity of soap, its structure previously identified as a long chain branched or normal carboxylic acid salt such as sodium, potassium, ammonium or substituted ammonium salt, present in the composition following the in situ generation of the free fatty carboxylic acid should be at a level wherein a surfactant effect, that is reduction of surface tension of water is achieved, when the composition is used to achieve removal of soil from skin. As used in this specification and claims, the numerical amounts of soap are those present after the formation of the in situ free fatty carboxylic acid. It is preferred to have at least about 1 wt. % soap present in the composition, generally about 5 wt.% is employed. Common quantities of soap for a "syndet" bar are about 10 wt. to 30 wt. % and a "combar" is about 55 to about 80 wt. %. Soap levels as high as about 90 to about 96 wt. % can be employed when a lower level of free fatty carboxyl acid is desired.

Other surfactants can be present in the composition as well. Examples of such surfactants are the anionic, amphoteric, nonionic and cationic surfactants. Examples of anionic surfactant include but are not limited to alkyl sulfates, anionic acyl sarcosinates, methyl acyl taurates, N-acyl glutamates, acyl isethionates, alkyl sulfosuccinates, alkyl phosphate esters, ethoxylated alkyl phosphate esters, trideceth sulfates, protein condensates, mixtures of ethoxylated alkyl sulfates and the like.

Alkyl chains for these surfactants are $C_8$–$C_{22}$, preferably $C_{10}$–$C_{18}$, more preferably $C_{12}$–$C_{14}$. Alkyl glycosides and methyl glucose esters are preferred mild non-ionics which may be mixed with other mild anionic or amphoteric surfactants in the compositions of this invention. Alkyl polyglycoside detergents are useful lather enhancers. The alkyl group can vary from about 8 to about 22 and the glycoside units per molecule can vary from about 1.1 to about 5 to provide an appropriate balance between the hydrophilic and hydrophobic portions of the molecule. Combinations of $C_8$–$C_{18}$, preferably $C_{12}$–$C_{16}$, alkyl polyglycosides with average degrees of glycosidation ranging from about 1.1 to about 2.7, preferably from about 1.2 to about 2.5, are preferred.

Anionic nonsoap surfactants can be exemplified by the alkali metal salts of sulfates and sulfonates having in their molecular structure an alkyl radical containing from about 8 to about 22 carbon atoms and a sulfonic acid or sulfuric acid ester radical (included in the term alkyl is the alkyl portion of higher acyl radicals). Preferred are the sodium, ammonium, potassium or triethanolamine alkyl sulfates, especially those obtained by sulfating the higher alcohols ($C_8$–$C_{18}$ carbon atoms), sodium coconut oil fatty acid monoglyceride sulfates and sulfonates; sodium or potassium salts of sulfuric acid esters of the reaction product of 1 mole of a higher fatty alcohol (e.g., tallow or coconut oil alcohols) and 1 to 12 moles of ethylene oxide; sodium or potassium salts of alkyl phenol ethylene oxide ether sulfate with 1 to 10 units of ethylene oxide per molecule and in which the alkyl radicals contain from 8 to 12 carbon atoms, sodium alkyl glyceryl ether sulfonates; the reaction product of fatty acids having from 10 to 22 carbon atoms esterified with isethionic acid and neutralized with sodium hydroxide; water soluble salts of condensation products of fatty acids with sarcosine; and others known in the art.

Zwitterionic surfactants can be exemplified by those which can be broadly described as derivatives of alphatic quaternary ammonium, phosphonium, and sulfonium compounds, in which the aliphatic radicals can be straight chain or branched and wherein one of the aliphatic substituents contains from about 8 to 18 carbon atoms and one contains an anionic water-solubilizing group, e.g., carboxy, sulfonate, sulfate, phosphate, or phosphonate. A general formula for these compounds is:

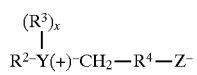

wherein $R^2$ contains an alkyl, alkenyl, or hydroxy alkyl radical of from about 8 to about 18 carbon atoms, from 0 to about 10 ethylene oxide moieties and from 0 to 1 glyceryl moiety; Y selected from the group consisting of nitrogen, phosphorus, and sulfur atoms; $R^3$ is an alkyl or monohydroxyalkyl group containing 1 to about 3 carbon atoms; X is 1 when Y is a sulfur atom and 2 when Y is a nitrogen or phosphorus atom, $R^4$ is an alkylene or hydroxyalkylene of from 0 to about 4 carbon atoms and Z is a radical selected from the group consisting of carboxylate, sulfonate, sulfate, phosphonate, and phosphate groups.

Examples include: 4-[N,N-di(2-hydroxyethyl)-N-octadecylammonio]-butane-1-carboxylate; 5-[S-3-hydroxypropyl-S-hexadecylsulfonio]-3 hydroxypentane-1-sulfate; 3-[P,P-P-diethyl-P 3,6,9 trioxatetradexocyl-phosphonio]-2-hydroxypropane-1-phosphate; 3-[N,N-dipropyl-N-3 dodecoxy-2-hydroxypropylammonio]-propanel-phosphonate; 3-(N,N-di-methyl-N-hexadecylammonio) propane-1-sulfonate; 3-(N,N-dimethyl-N-hexadecylammonio)-2-hydroxypropane-1-sulfonate; 4(N,N-di(2-hydroxyethyl)-N-(2 hydroxydodecyl) ammonio]-butane-1-carboxylate; 3-[S-ethyl-S-(3-dodecoxy-2-hydroxypropyl)sulfonio]-propane-1-phosphate; 3-(P,P-dimethyl-P-dodecylphosphonio)-propane-1-phosphonate; and 5-[N,N-di(3-hydroxypropyl)-N-hexadecylammonio]-2-hydroxy-pentane-1-sulfate.

Examples of amphoteric surfactants which can be used in the compositions of the present invention are those which can be broadly described as derivatives of aliphatic secondary and tertiary amines in which the aliphatic radical can be straight chain or branched and wherein one of the aliphatic substituents contains from about 8 to about 18 carbon atoms and one contains an anionic water solubilizing group, e.g., carboxy, sulfonate, sulfate, phosphate, or phosphonate. Examples of compounds falling within this definition are sodium 3-dodecylaminopropionate, sodium 3-dodecylaminopropane sulfonate, N-alkyltaurines, such as the one prepared by reacting dodecylamine with sodium isethionate according to the teaching of U.S. Pat. No. 2,658,072, N-higher alkyl aspartic acids, such as those produced according to the teaching of U.S. Pat. No. 2,438, 091, and the products sold under the trade name "Miranol" and described in U.S. Pat. No. 2,528,378. Other amphoterics such as betaines are also useful in the present composition.

Examples of betaines useful herein include the high alkyl betaines such as coco dimethyl carboxymethyl betaine, lauryl dimethyl carboxy-methyl betaine, lauryl dimethyl alpha-carboxyethyl betaine, cetyl dimethyl carboxymethyl betaine, lauryl bis-(2-hydroxyethyl)carboxy methyl betaine, stearyl bis-(2-hydroxypropyl) carboxymethyl betaine, oleyl dimethyl gamma-carboxypropyl betaine, lauryl bis-(2-hydro-xypropyl) alpha-carboxyethyl betaine, etc. The sulfobetaines may be represented by coco dimethyl sulfopropyl betaine, stearyl dimethyl sulfopropyl betaine, amido betaines, amidosulfobetaines, and the like.

Many cationic surfactants are known to the art. By way of example, the following may be mentioned:
stearyldimenthylbenzyl ammonium chloride;
dodecyltrimethylammonium chloride;
nonylbenzylethyldimethyl ammonium nitrate;
tetradecylpyridinium bromide;
laurylpyridinium chloride;
cetylpyridinium chloride;
laurylpyridinium chloride;
laurylisoquinolium bromide;
ditallow(Hydrogenated)dimethyl ammonium chloride;
dilauryldimethyl ammonium chloride; and
stearalkonium chloride.

Additional cationic surfactants are disclosed in U.S. Pat. No. 4,303,543 see column 4, lines 58 and column 5, lines 1–42, incorporated herein by reference. Also see CTFA Cosmetic Ingredient Dictionary, 4th Edition 1991, pages 509–514 for various long chain alkyl cationic surfactants; incorporated herein by references.

Also present in the composition may be the standard agents found in these compositions such as fragrances, colorants, further preservatives, thickeners, electrolytes, pH adjusting agent and the like.

The composition can take on the usual physical forms a personal care cleansing composition has, such as solid, gel or liquid. A solid material can have a minimum water content of about 2–3 wt. % or a substantially higher content for example, about 25 to 26 wt. %, or quantities in between these amounts such as about 7 to about 15 wt. %. The pH of such a composition can be from about 5 to about 11 as measured by pH meter of a 1% solid product solution in water. The inventive compositions are chelating effective and temperature stable at alkaline pH. Such solid compositions generally take the form of a bar that is readily held in the hand. The bar is usually opaque but can be translucent or transparent.

Liquid formulations are usually aqueous and have anywhere from about 10 to about 95 wt. % water. Compatible thickening agents can be added to the composition to obtain the desired viscosity. Gels can be made although usually an appropriate viscosity of a liquid soap is one that is readily hand pumpable from a container.

Below are examples of the invention, examples used for comparative purposes and preparation and test procedures. The indicated examples are not intended to narrow but merely exemplify the broad inventive concept.

Soap samples were prepared by the following procedure:

Sodium Soap (3978 gms, moisture=29.35%, the rest long chain alkyl with 70 wt. % alkyl obtained from tallow/30 wt. % alkyl obtained from coconut oil) was melted (80° C.) in a crutcher equipped with a stirrer. Ferric sulfate (10 ppm), copper sulfate (1 ppm) and t-butylhydroxytoluene (BHT) (200 ppm) were added to the soap followed by the in-situ fattening agent being studied—citric acid or PPTC or PBCA (23.73 gm). Sufficient amount of in situ fattening agent was added to fully neutralize free alkali present in soap (0.01–0.15 wt. percent sodium oxide) as well as to generate a certain quantity of free fatty acids. The contents in the crutcher were mixed for 30 minutes. The soap chips were then made by drying the soap to approximately 12–13% moisture.

The soap chips were then mixed with perfume and titanium dioxide in an amalgamator at 25°–30° C., milled three times, plodded and pressed into soap bars.

Extraction of Free Fatty Acids

Soap chips prepared with PBCA, PPTC and citric acid were dried in a vacuum oven at 80°–85° C. and 25 inch Hg pressure. Fatty acids were extracted for 8–10 hours with dry acetone. The extracted fatty acids were dried to constant weight. The fatty acids were titrated with sodium hydroxide for % free fatty acids. The composition of fatty acids were determined by gas chromatography. All of the experiments were done in triplicate. Below are the results:

IV. Composition of Fatty Acids Generated by In-Situ Superfatting Soap Base: wt. percent

|  | | Acidulating Agent | |
| --- | --- | --- | --- |
| C-Chain | Citric Acid | PBCA | PPTC |
| C8 | 2.3 | 2.3 | 2.3 |
| C10 | 1.2 | 1.1 | 1.3 |
| C12 | 12.0 | 11.0 | 13.1 |
| C14 | 4.3 | 4.0 | 4.7 |
| C16 | 11.6 | 12.5 | 10.7 |
| C18 | 7.8 | 8.8 | 6.7 |
| C18:1 | 48.0 | 49.2 | 46.8 |
| :2 | 5.4 | 5.3 | 5.6 |
| :3 | 0.5 | 0.4 | 0.6 |
| Others | | | |
| MW | 261 | 262 | 260 |
| Iodine Value (IV)* | 57 | 57 | 56 |

*AOCS Official Methods Da 15–48

These results show that the free fatty acid spectrum produced by citric acid, PPTC and PBCA are similar.

Following the procedure above, soap samples were prepared with no in situ fatting agent (Example 1), citric acid in sufficient quantity to product 2 wt. % of free fatty acid in the composition (Example 2), PPTC in sufficient quantity to produce 1 wt. % of free fatty acid in the composition (Example 3), and PBCA in sufficient quantities to produce 1.5 wt. % of free fatty acid in the composition (Example 4).

The induction time for the occurrence of oxidation of the soaps was measured by a rapid oxidative stability evaluation method. The samples were dried in a vacuum oven for approximately 2 hours at 170° F. At the start, the vacuum oven was flushed with nitrogen. The final moisture content of the samples was adjusted to approximately 10%.

A DuPont 9900 Thermal Analyzer with 912 (DSC) Module and Pressure Dual Sample Cell was used for all the samples.

The soap chips were weighed (5–10 mg) in an open aluminum pan. The pan was then positioned on top of the "dimples" in the pressure cell. Two samples can be simultaneously tested in the dual cell. The pressure cell was assembled. The cell was purged with oxygen gas twice, and then pressurized to 200psi. The samples were heated to 135° C. for 70/30 tallow alkyl/coco alkyl soap chips in the differential scanning calorimetry (DSC) cell. Induction times for the oxidation of the samples were measured isothermally. The onset of oxidation of the soap sample was indicated by a positive deviation from the baseline. The induction time of oxidation was determined by extrapolation of the base line and the leading slope of the peak. The longer the induction time the more stable the system.

Below are the results

| Example | Induction Time/ Minutes |
| --- | --- |
| 1 (no stabilizing agent) | 13.3 |
| 2 (citric acid) | 34.1 |
| 3 (PPTC) | 40.0 |
| 4 (PBCA) | 98.1 |

Both the PPTC and PBCA provided greater oxidative stability to the system than citric acid. PBCA is preferred. The PPTC and PBCA were present in quantities which generated less free fatty acid than the citric acid. Clearly on a molar basis both the PPTC and PBCA were far more effective in stabilizing the system than citric acid.

We claim:

1. A personal cleansing composition comprising:

a. at least about one wt % of soap, and b. a sufficient amount of a compound to provide at least about 0.03 wt. % of a free fatty carboxylic acid, said compound of the formula

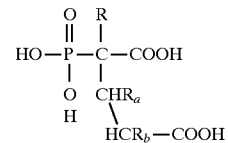

wherein R is hydrogen or $CH_2COOH$, $R_a$ is hydrogen or carboxyl, and $R_b$ is hydrogen provided that when R is hydrogen, then $R_a$ is carboxyl and when R is $CH_2COOH$ then $R_a$ is hydrogen, "the composition as a solid bar which can be hand be held."

2. A method of cleansing the face and hands which comprises applying to the face and hands and rinsing with water a composition comprising a. at least about 1 wt. % of soap, and b. a sufficient amount of a compound to provide at least about 0.03 wt. % of a free fatty carboxylic acid, said compound of the formula

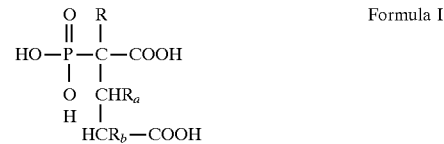

Formula I wherein R is hydrogen, or $CH_2COOH$ and $R_a$ is hydrogen or carboxyl, and $R_b$ is hydrogen or methyl provided that when R is hydrogen then $R_a$ is carboxyl and when R is $CH_2COOH$ then is hydrogen.

3. The method in accordance with claim 2 wherein $R_b$ is hydrogen.

4. The method in accordance with claim 3 wherein R is hydrogen.

5. The method in accordance with claim 3 wherein R is $CH_2COOH$.

6. The method in accordance with claim 3 wherein a flavorant is absent or less than a soap masking quantity of flavorant is present.

7. The method in accordance with claim 2 wherein from about 5 to about 96 wt. % of soap is present.

8. The method in accordance with claim 6 wherein from about 5 to about 96 wt. % of soap is present.

9. The method in accordance with claim 7 wherein R is hydrogen.

10. The method in accordance with claim 8 wherein R is $CH_2COOH$.

11. The method in accordance with claim 3 wherein the composition is in solid form.

12. The method in accordance with claim 11 wherein the solid form is in the shape of a bar which can be hand held.

13. The method in accordance with claim 12 where water is present from about 2 to about 16 weight percent of the composition.

14. The method in accordance with claim 2 wherein R is CH2COOH.

15. The method in accordance with claim 14 wherein a flavorant is absent or less than a soap masking quantity of flavorant is present.

16. The method in accordance with claim 15 wherein from about 5 to about 96 wt. % of soap is present in the composition.

17. The method in accordance with claim 16 wherein from about 10 to 30 wt. % of soap is present or from about 55 to 80 wt. % of soap is present in the composition.

18. A personal cleansing composition comprising a. at least about 5 wt. % of soap, and b. a sufficient amount of a compound to provide at least about 0.03 wt. % of a free fatty carboxlic, said compound of the formula

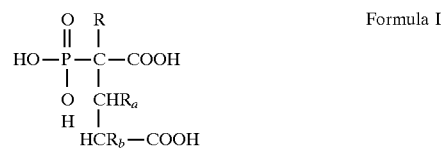

Formula I wherein R is $CH_2COOH$, $R_a$ is hydrogen and $R_b$ is hydrogen.

* * * * *